United States Patent [19]

Stapp

[11] 4,221,917
[45] Sep. 9, 1980

[54] PRODUCTION OF ESTERS FROM MONOOLEFINS AND DIOLEFINS

[75] Inventor: Paul R. Stapp, Bartlesville, Okla.

[73] Assignee: Phillips Petroleum Company, Bartlesville, Okla.

[21] Appl. No.: 883,012

[22] Filed: Mar. 3, 1978

[51] Int. Cl.$^2$ ............................................. C07C 67/05
[52] U.S. Cl. .................................. 560/246; 260/410.6; 260/464; 260/465 D; 260/465.4; 560/1; 560/80; 560/83; 560/84; 560/87; 560/89; 560/106; 560/112; 560/122; 560/126; 560/139; 560/145; 560/183; 560/192; 560/193; 560/197; 560/198; 560/228; 560/229; 560/230; 252/426; 252/429 R
[58] Field of Search ............... 560/246, 112, 1, 80, 560/83, 84, 87, 89, 106, 122, 126, 139, 145, 183, 192, 193, 197, 198, 228, 229, 230; 260/410.6, 464, 465 D, 465.4

[56] References Cited

U.S. PATENT DOCUMENTS

| | | | |
|---|---|---|---|
| 2,467,231 | 4/1949 | Richards | 260/83 |
| 3,376,285 | 4/1968 | Callihan | 260/232 |
| 3,770,813 | 11/1973 | Kollar | 560/246 |
| 3,803,133 | 4/1974 | Vogt | 260/239.55 D |
| 4,000,185 | 12/1976 | Kurkov | 560/246 |
| 4,045,477 | 8/1977 | Sherwin | 560/246 |
| 4,061,868 | 12/1977 | Fumagalli | 560/246 |
| 4,087,623 | 5/1978 | Sherwin | 560/246 |

OTHER PUBLICATIONS

Hill, Chem, Rev. 61, pp. 537–562 (1961).
Cregee, Justus Liebigs Annalen der Chemie, 541, pp. 218–238 (1939).

*Primary Examiner*—Natalie Trousof
*Assistant Examiner*—Michael Shippon

[57] ABSTRACT

Monoolefins and diolefins are converted to corresponding esters in a process by contacting together at least one monoolefin, diolefin or mixture thereof, oxygen, at least one iodosoaryl dicarboxylate and at least one carboxylic acid, carboxylic acid anhydride or mixture thereof.

64 Claims, No Drawings

PRODUCTION OF ESTERS FROM MONOOLEFINS AND DIOLEFINS

BACKGROUND OF THE INVENTION

The invention relates to a process for the production of esters. In one aspect, the invention relates to a process for the oxidation of monoolefins and diolefins.

It is desirable to oxidize monoolefins and diolefins to produce diesters. Such diesters are well known in the art and they are particularly useful as chemical intermediaries for the production of saturated diols.

For example, it is desirable to oxidize conjugated diolefins, such as 1,3-butadiene and/or 2-methyl-1,3-butadiene to produce various compounds such as the ethylenically unsaturated esters. An example is the oxidation of 1,3-butadiene to produce 1,4-diacetoxy-2-butene. The diacetoxybutene is then easily converted, by processes well known in the art, to other compounds such as tetrahydrofuran or 1,4-butanediol. Although there are various processes and catalysts known which are useful for the oxidation of monoolefins and diolefins, most of these processes are relatively expensive to carry out. Therefore, new processes are desirable in an effort to more fully develop the art and improve the overall process.

An object of the present invention is to oxidize monoolefins and diolefins to produce diesters.

Another object of the invention is to oxidize monoolefins and diolefins to produce diesters using a process that consumes the various reactants efficiently.

Other objects, advantages and aspects of the present invention will be apparent to those skilled in the art after studying the specification and appended claims.

SUMMARY OF THE INVENTION

According to the invention a diester is produced from at least one monoolefin, diolefin or mixture thereof by contacting together the olefin in the reactant, oxygen, at least one iodosoaryl dicarboxylate and at least one carboxylic acid, carboxylic acid anhydride or mixture thereof, under reaction conditions. The invention provides an efficient and effective way to produce a diester from an olefin in reactant.

DETAILED DESCRIPTION OF THE INVENTION

The present invention, at least in part, is based upon the discovery that in a reaction employing an iodosoaryl dicarboxylate compound and an olefin to produce a diester, it is not necessary to employ the iodosoaryl dicarboxylate compound in stoichiometric amounts provided oxygen and a carboxylic acid and/or a carboxylic acid anhydride are present in the reaction mixture. In an article entitled "Iodoso Compounds as Oxidizing Agents" by Rudolf Criegee and Hans Beucher published in Justus Liebigs Annalen der Chemie 541, pages 218 to 328 (1939) the oxidation of a variety of olefinic compounds using a number of iodoso acetates including phenyliodoso acetate was disclosed. Specifically, cyclopentadiene was oxidized with phenyliodoso acetate in the presence of a glacial acetic acid to produce diacetoxy derivatives of cyclopentene. The reference discloses that the phenyliodoso acetate was employed in stoichiometric amounts as compared to the present invention in which stoichiometric amounts of the iodoaryl dicarboxylate compound are not required. The reference does not disclose the use of oxygen in the reaction mixture. Further while the iodoaryl dicarboxylate compound is consumed in the present invention it is also regenerated during the reaction so that the net result is that the same amount of iodoaryl dicarboxylate is present in the reaction mixture at the end of the reaction as in the beginning of the reaction. Thus in some respects the iodosoaryl dicarboxylate compound resembles a catalyst when employed to produce diesters in accordance with the invention.

The olefinic reactants converted to diesters according to the process of the invention are selected from acyclic or cyclic monoolefins and diolefins. While mixtures of two or more of either or both of these can be employed, preferably and usually single species are employed to limit subsequent purification steps.

The monoolefins can be either acyclic or cyclic, substituted or unsubstituted, and there does not appear to be any operability limitation on molecular size other than convenience and availability.

The acyclic monoolefins, preferably of 2 to about 16 carbon atoms per molecule for convenience and availability, correspond to the general formula:

The cyclic monoolefins, preferably of 4 to 16 carbon atoms per molecule for convenience and availability, correspond to the general formula:

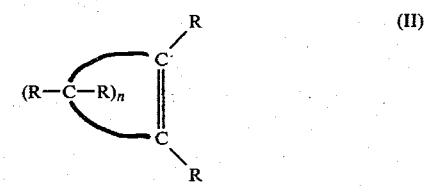

The diolefins can be either acyclic or cyclic, substituted or unsubstituted, and there does not presently appear to be any limitation on molecular size except convenience and availability. When diolefins are employed they generally are conjugated diolefins because diesters produced from conjugated diolefins are substantially more in demand; however, the invention can be practical with nonconjugated diolefins. While in the broadest aspect of this invention diolefins generally can be employed, acyclic and cyclic conjugated diolefins are usually employed.

The acyclic conjugated diolefins, preferably of 4 to 16 carbon atoms per molecule for convenience and availability, correspond to the general formula:

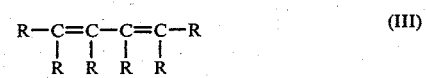

The cyclic conjugated diolefins, preferably of 5 to 16 carbon atoms per molecule for convenience and availability, correspond to the general formula:

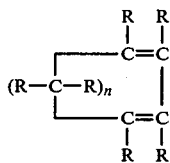

(IV)

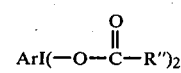

(V)

In each of the above formulae, each R is individually selected from hydrogen, halogen, cyano, —COOR', and a hydrocarbyl radical containing preferably 1 to 12 carbon atoms and which can be alkyl, aryl, cycloalkyl, or combination thereof such as aralkyl, alkaryl, or the like. When R is an aryl radical it can be a polycyclic radical or a monocyclic radical. R' is hydrogen, or an alkyl radical of preferably 1 to 10 carbon atoms or aryl radical of preferably 6 to 10 carbon atoms and n is an integer of preferably 1 to 14, within the carbon atom limitations described.

Exemplary acyclic monoolefins include ethylene, propylene, 1-butene, 2-butene, 1-hexene, 2-octene, 1-decene, 3-dodecene, 1-hexadecene, 2,3-dimethyl-2-butene, 1,1-diphenylethylene, 1-chloro-2-butene, 3-butenenitrile, ethyl cinnamate, and mixtures of any two or more thereof. Exemplary cyclic monoolefins include vinylcyclohexane, cyclobutene, cyclopentene, cyclohexene, cycloheptene, cyclooctene, cyclododecene, 1-methyl-1-cyclopentene, 1-phenyl-1-cyclohexene, ethyl 1-cyclohexene-1-carboxylate, 1,3,4,5,6-pentachlorocyclohexene, 1-cyano-1-cyclohexene, and mixtures of any two or more thereof.

Some examples of suitable nonconjugated diolefins useful in the invention include: 1,5-hexadiene, 1,7-octadiene, 1,9-decadiene, 1,4-cyclohexadiene, 1,5-cyclooctadiene, 1,5-cyclododecadiene and mixtures of any two or more thereof.

Exemplary acyclic conjugated diolefins include: 1,3-butadiene, 2-methyl-1,3-butadiene, 2-chloro-1,3-butadiene, 2-ethyl-1,3-butadiene, 2-cyano-1,3-butadiene, 2-methylene-3-butenoic acid, 2,4-pentadienenitrile, 1,3-hexadecadiene, 2-methoxy-carbonyl-1,3-butadiene, 2-decycloxycarbonyl-1,3-butadiene, 2-phenoxycarbonyl-1,3-butadiene, 2-(1-naphthyloxy)carbonyl-1,3-butadiene, 2-benzyl-1,3-butadiene, 2-p-tolyl-1,3-butadiene, 2-chloro-3-methyl-1,3-butadiene, and mixtures of any two or more thereof.

Exemplary of the cyclic conjugated diolefins include 1,3-cyclohexadiene, 1,3-cyclooctadiene, 1,3-cyclododecadiene, 5-methyl-1,3-cyclohexadiene, 2,4-cyclohexadiene-1,2-dicarboxylic acid, octafluoro-1,3-cyclohexadiene, hexachlorocyclopentadiene, 5,6,7,8-tetrabromo-1,3-cyclooctadiene, 2-cyclohexyl-1,3-butadiene, 1,3-cyclohexadecadiene, 2-undecyl-1,3-cyclopentadiene, 2-methoxycarbonyl-1,3-cyclooctadiene, 2-decycloxycarbonyl-1,3-cyclopentadiene, 2-phenoxycarbonyl-1,3-cyclohexadiene, 2-(1-naphthyloxy) carbonyl-1,3-cyclopentadiene, 2-benzyl-1,3-cyclooctadiene, 2-p-tolyl-1,3-cyclohexadiene, and mixtures of any two or more thereof.

It is preferably preferred that both the monoolefin reactant or the diolefin reactant contain only carbon and hydrogen because of availability and reactivity considerations.

The compound employed in the present invention to convert an olefin to the desired diacyloxy compound is represented by the following general formula:

wherein Ar— has from 6 to 12 carbon atoms and is a monocyclic or dicyclic aryl hydrocarbon radical or a substituted monocyclic or dicyclic aryl radical wherein the substituent or substituents on the substituted aryl radical are selected from the group consisting of alkyl, cycloalkyl, halo, carbalkoxy and cyano groups. The dicyclic aryl radicals suitable for use in the invention are those which join monocyclic aryl radicals with only one carbon-carbon single bond, such as biphenyl radicals. Condensed polycyclic aryl radicals such as naphthyl radicals or substituted derivatives thereof are not intended to be included within the scope of suitable Ar— radicals according to the instant invention. It is believed that radicals such as naphthyl radicals are too easily oxidized under the reaction conditions of this invention and thus effectively become unable to serve as suitable agents for the reaction of the instant invention. Examples of suitable Ar— radicals according to the definition provided above include phenyl, 4-methylphenyl, 4-hexylphenyl, 4-cyclohexylphenyl, 4-cyanophenyl, 4-chlorophenyl, 4-carbethoxyphenyl, 4-biphenyl, 3-biphenyl, 2-biphenyl, 3-isopropylphenyl, 3-bromophenyl, 4-fluorophenyl, 3-iodophenyl, and 3-cyano-4-methylphenyl. R''— is selected from the group of $C_1$–$C_{17}$ radicals consisting of alkyl, aryl, cycloalkyl or combinations such as alkaryl, aralkyl, cycloalkylaryl, and the like, or halogen-, cyano-, or —COOR'' substituted derivatives thereof, wherein up to 4 of said halogen, cyano, or —COOR'' substituents can be present in said radical. The group R'— has the same meaning as that given in the discussion of the general formula I through IV above.

Some suitable iodosoaryl dicarboxylate compounds for use in the invention include: iodosobenzene diacetate, iodosobenzene di-hexanoate, iodosobenzene didodecanoate, iodosobenzene di(trichloroacetate), iodosobenzene di(4-cyanobenzoate), iodoso-4,4'-biphenyl diacetate, iodoso-4-cyclohexylphenyl diacetate, iodoso-3-isopropylphenyl diacetate, iodoso-3-bromophenyl diacetate, iodoso-3-cyano-4-methyl-phenyl diacetate, iodoso-4-methylphenyl diacetate, iodoso-4-cyanophenyl diacetate and mixtures of any two or more thereof.

Methods of preparation of an iodosoaryl dicarboxylate compound are known in the art. One convenient method of preparation involves the oxidation of aryl iodides in the presence of carboxylic acids. Since the reaction of the instant invention is carried out under suitable oxidizing conditions, a further embodiment according to the instant invention is to carry out the reaction of the monoolefin and/or diolefin described above in the presence of a suitable aryl iodide, ArL, a suitable carboxylic acid, and oxygen. In this embodiment, the reactive compound, the iodosoaryl dicarboxylate, is generated in situ. As indicated in the examples which will be given below, the reaction mixture provides recoverable amounts of the aryl iodide, ArL. Thus, a cyclic process can be carried out according to one aspect of the instant invention wherein the initial charge to the reaction mixture includes either the preformed iodosoaryl dicarboxylate or a mixture of an aryl iodide and a carboxylate acid and the recovered aryl iodide is recycled in the presence of or with the addition of additional carboxylic acid to regenerate the reactive compound.

As a third embodiment for the process of the instant invention, the reactive compound, iodosoaryl dicarboxylate, is generated from the reaction of an aryl hydrocarbon, elemental iodine, and a suitable carboxylic acid in the presence of oxygen. This embodiment is possible because the reaction of elemental iodine with the aryl hydrocarbon in the presence of oxygen produces aryl iodide which in turn reacts with the carboxylic acid under oxidizing conditions to give the desired iodosoaryl dicarboxylate.

In an optional but preferred embodiment of the instant invention, the reaction system is utilized in the presence of a source of bromide ion, preferably alkali metal bromides, in order to give enhanced yields of the desired diacyloxy olefins. The alkali metal bromides are preferred because they are readily available and produce good results. In this embodiment, the molar ratio of bromide ion to aryl iodide or its equivalent is sufficient to provide enhanced yields of the desired diacyloxy olefins; generally said molar ratio is within a range from about 1/1 to about 5/1. Laboratory results indicate that good results can be expected employing the alkali metal bromide within a range of from about 2/1 to about 4/1. Suitable sources of bromide ion include lithium bromide, sodium bromide, potassium bromide, and rubidium bromide.

The reaction of the instant invention is an oxidation reaction and as such is carried out in the presence of free molecular oxygen. The amount of oxygen present is not believed to be critical though it is recognized that an undesirably slow reaction will result if the concentration of oxygen is very low. Essentially pure oxygen can be employed as well as mixtures of oxygen with inert gases or ambient air can be employed as a source of free oxygen for the instant reaction.

It is recognized that explosive conditions could be obtained if the amount of oxygen added to the reaction system is not under control. The reaction of this invention, as is true with many oxidation reactions, appears to be highly exothermic and this too indicates caution in adding oxygen to the system. Because of these considerations, it is desirable to add the oxygen incrementally or continuously during the reaction to avoid an explosive range of oxygen concentration and to allow better control of the temperature of the reaction. A reaction vessel with efficient mixing means is also desirable to avoid build-up of dangerous concentrations of free oxygen.

The process can be carried out under an oxygen pressurization over a broad range, so long as sufficient oxygen is provided to be effective in the oxidation reactions, not cause unduly long times of reaction, and at the same time not be so unduly high in concentration as to provide unduly hazardous conditions. An exemplary broad range of oxygen pressure is about 0.1 to 1,000, presently preferably about 5 to 200, psig of oxygen above autogenous pressure at the temperature employed.

The reactions of the process can be carried out over a broad temperature range, so long as the temperature is sufficient to provide suitable reactivity of the reactants, and not so high as to be unduly hazardous. Exemplary temperatures lie in the range of about 70° C. to 170° C., presently preferably about 90° C. to 150° C.

The reaction time can be selected over a relatively wide range, as desired or convenient. The overall reaction time depends on the temperature, catalyst activity, and oxygen pressure employed. An exemplary range is about 1 minute to about 12 hours.

The carboxylic acid suitable for use in accordance with the invention is represented by the general formula $$R''-COOH \qquad (VI)$$

wherein R" is as defined previously in Formula V. Furthermore, said carboxylic acid is generally selected from those containing from about 2 to about 18 carbon atoms per molecule. Carboxylic acid anhydrides corresponding to the above described acids are also suitable for use in the invention alone or in mixtures with such acids.

Acetic acid is a presently preferred carboxylic acid for use in accordance with the instant invention because of cost and availability. Examples of suitable carboxylic acids include acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, 2-bromobutanoic acid, 4-chlorobenzoic acid, 4-cyanobenzoic acid, 2,3,4,5-tetrachlorobenzoic acid, and mixtures of any two or more thereof. When the free carboxylic acid is employed, the amount of carboxylic acid present should be at least equal to and preferably greater than a mole ratio of 2/1 in terms of the aryl iodide or the substituted or unsubstituted aryl compound. It is generally convenient to employ the carboxylic acid as the reaction diluent for the process of this invention. In such instances, a large excess of the carboxylic acid to the aryl iodide or substituted or unsubstituted aryl compound is present. The carboxylic acid present in the reaction mixture either as carboxylic acid initially or as a carboxylic acid anhydride provides the acyl moiety of the diacyloxy olefine in the final product. In most instances, it is desirable to employ as part of the reaction mixture, the corresponding carboxylic anhydride (in addition to the carboxylic acid), as an optional preferred component. The use of a carboxylic anhydride serves to simplify the purification and separation steps by reducing the amount of by-products which contain free hydroxy groups. When employed, the carboxylic anhydride is generally at least in a mole ratio of 2/1 to the olefinic reactant. Usually the mole ratio of carboxylic anhydride to olefinic reactant is within a range of from about 2/1 to about 5/1.

Other diluents can be employed in the process of the instant invention along with the carboxylic acids. For example, such compounds as benzene, sulfolane, cyclohexane, chlorobenzene, methylbenzoate, toluene and the like can be utilized along with at least one carboxylic acid, carboxylic acid anhydride and mixtures thereof as reaction diluents in the process of the instant invention.

The reaction mixtures obtained according to the process of this invention are generally vented to remove any unreacted oxygen and olefin and then distilled to remove any free carboxylic acid or anhydride or other diluent which may be present. The product mixture remaining is usually fractionally distilled to recover one or more fractions containing the diacyloxy olefins. As noted above, the aryl iodide can be recovered also from the reaction mixture and can be recycled to the reaction zone directly in accordance with one embodiment of the invention or the aryl iodide can be reacted separately in the presence of carboxylic acid and oxygen to generate the aryl iodosocarboxylate which is then charged to the reaction zone. Any unreacted olefin recovered from the reaction mixture can also be recycled to the reaction zone as desired. Various isomers of the desired diester recovered from the product mixture can be recycled to the reaction zone for conversion to the more desired 1,4 isomer. For example, where 1,3-butadiene is converted to 1,4-diacyloxy butene, 1,2-diacyloxy butene is also produced which can be recycled to the reaction zone.

While the invention relates to the production of diesters from monoolefins and diolefins, the invention is particularly suitable for converting conjugated diolefins to 1,4-diacyloxy olefins which have utility as intermediates for the preparation of the corresponding saturated diols, such as for example, 1,4-butanediol. In addition, British Pat. No. 1,170,222 describes the preparation of tetrahydrofurans, starting with conjugated diolefins and proceeding through the 1,4-diacyloxy butenes. Tetrahydrofuran itself, of course, would be produced starting with 1,3-butadiene.

The reaction mixtures of the instant invention appear to be particularly corrosive to certain metals commonly used in chemical reactors, i.e., iron or steel or chromium type metals appear to be corroded to a significant extent by the reaction mixtures of this invention. In addition, the compounds formed from iron or chromium by means of the corrosion process appear to give rise to undesirable side reactions. Therefore, it is desirable that the reaction of the instant invention be carried out in a glass-lined reactor or in reactors which are protected by chemically resistant coatings or in reactors having linings of tantalum or titanium or other essentially inert metals.

EXAMPLES

EXAMPLE I

Two runs were conducted according to the instant invention wherein 1,3-butadiene was oxidized with iodosobenzene diacetate in the presence of molecular oxygen. In each of these runs, a 250 ml Fisher-Porter aerosol compatibility bottle equipped with a magnetic stirring means served as the reaction vessel. In each run, the reaction vessel was charged with 6.4 grams (20 mmoles) of iodosobenzene diacetate, 50 ml of acetic acid, and 25 ml of acetic anhydride. In run No. 1, 10.2 grams (188.9 mmoles) of butadiene was charged in the vapor phase while in run No. 2, 11.3 grams (209.2 mmoles) of butadiene was charged in the vapor phase. In each run, the bottle reactor was then placed in an oil bath, pressured to 30 psig with oxygen and heated to 140° C. in the case of run No. 1 while the reaction temperature was 100° C. for reaction No. 2. About 0.75–1.5 hours was required to reach the desired reaction temperature. During each reaction run, the reaction vessel was pressured to 120 psig with oxygen to about 20 minute intervals during the course of the run. Each run was carried out for a period of about 4.75 hours. At the conclusion of each run, the reaction vessel was cooled briefly, then vented and weighed to determine the weight gain of the reactor contents during the reaction period. Each reaction mixture was transferred to a distillation flask and distilled through an 18″ Vigreaux column under reduced pressure. Two fractions were collected with the first fraction boiling at 49°–60° C. at 60 millimeters mercury pressure comprising predominantly the excess acetic acid and acetic anhydride. The second fraction in each case was obtained at 6 millimeters mercury pressure with a boiling range of 50°–115° C. In each instance, the second fraction thus obtained was analyzed by gas-liquid phase chromatography to determine the amount of diacetoxy butenes (DAB) which were obtained. It was also found by the gas-liquid phase chromatography that the second fraction contained from 17–20 percent by weight of iodobenzene. The results obtained in these two runs are summarized below in Table I.

TABLE I

| Run No. | Temp. °C., | Mmole, DAB | | | | % Yield[d] DAB |
|---|---|---|---|---|---|---|
| | | 1,2-[a]; | cis-1,4-[b]; | trans-1,4-[c] | Total Mmole | |
| 1 | 140 | 28.2 | 0.9 | 7.7 | 36.8 | 19.5 |
| 2 | 100 | 26.6 | 2.2 | 8.5 | 37.3 | 17.8 |

[a]1,2-diacetoxy-3-butene.
[b]cis-1,4-diacetoxy-2-butene.
[c]trans-1,4-diacetoxy-2-butene.
[d]Based on the amount of 1,3-butadiene charged.

The results shown in Table I demonstrate that the instant invention provides a process for producing diacetoxy butenes by the oxidation of 1,3-butadiene with iodosobenzene diacetate in the presence of oxygen. The iodosobenzene diacetate in effect acts as a catalyst as indicated by the results shown in Table I in that the amount of diacetoxy butenes produced is more than 1.5 times the amount of iodosobenzene diacetate charged to the reaction mixture.

EXAMPLE II

Other runs were conducted utilizing the same type of reaction vessel described in the runs of Example I. In the invention (Run No. 3) of this Example, another embodiment of the process of the instant invention was demonstrated. Specifically, in run No. 3 the reaction was carried out utilizing iodobenzene in the presence of acetic acid and acetic anhydride for the oxidation of 1,3-butadiene to the diacetoxy butenes. In addition, the inventive run also utilized the presense of lithium bromide as a yield promoting reagent according to the instant invention. In run No. 3, the reaction vessel was charged with 6.5 grams (75 mmoles) of lithium bromide, 4.1 grams (20 mmoles) of iodobenzene, 50 ml of acetic acid, 25 ml of acetic anhydride, and 12.8 grams (237 mmoles) of butadiene in the vapor phase.

Run No. 4 was a control run wherein in addition to iodobenzene there was charged cupric acetate monohydrate to the reaction system. In this run, the reactor was charged with 4.1 grams (20 mmoles) of iodobenzene, 4.8 grams (24 mmoles) of the cupric acetate monohydrate, 50 ml of acetic acid, 25 ml of acetic anhydride, and 14 grams (259.3 mmoles) of butadiene from the vapor phase.

Run No. 5 was another control run wherein boric acid was charged to the reaction mixture with the iodobenzene. In this run, the reactor was charged with 4.0 grams (20 mmoles) of iodobenzene, 1.2 grams (20 mmoles) of boric acid, 50 ml of acetic acid, 25 ml of acetic anhydride, and 12.5 grams (231.5 mmoles) of butadiene from the vapor phase.

In each of runs 3–5, the reactor was placed in an oil bath, pressured to 30 psig with oxygen and heated to 140° C. About one hour was required for the reactor to reach the desired temperature. As in the previous runs of Example I, the reaction mixture was pressured to about 120 psig with oxygen at about 20 intervals throughout the course of the reaction period. At the end of the reaction period, the reaction vessel was cooled along with other reaction conditions which were utilized in the runs.

TABLE III

| Run No. | Promoter, (mmole) | Time, Hrs. | Bd (mmole) | HoAc ml. | Ac₂O ml. | mmole DAB Total | % Yield DAB |
|---|---|---|---|---|---|---|---|
| 6 | LiBr (75) | 3.5 | 196.3 | 50 | 25 | 77.8 | 39.6 |
| 7 | LiBr (150) | 4 | 222.2 | 50 | 25 | (a) | — |
| 8 | LiBr (75) | 5.5 | 203.7 | 0 | 75 | (b) | — |
| 9 | LiOAc (75) | 4.5 | 198.1 | 0 | 100 | 36.4 | 18.4 |
| 10 | V₂O (5) | 6 | 231.5 | 0 | 100 | (c) | — |
| 11 | V₂O (5) | 5.5 | 220.4 | 0 | 100 | (d) | — |

(a)Reaction mixture discarded since little, if any, oxidation took place.
(b)No analysis made of 12 g fraction from distillation.
(c)No analysis made. Accident during work-up.
(d)No analysis made of 15 g brown oily residue from reaction mixture.

briefly, vented and then weighed to record the weight gain of the reaction mixture. The mixtures were filtered, in each instance, from any solid materials that were present and distilled as previously described through an 18" Vigreaux column under reduced pressure. The fraction comprising the diacetoxy butenes was analyzed by gas-liquid phase chromatography as previously described in Example I. The results obtained in runs 3-5 of this Example are presented in Table II below.

TABLE II

| Run No. | Time Hrs. | Mmole, DAB 1,2-; | cis-1,4-; | trans-1,4- | Total mmole | % Yield DAB |
|---|---|---|---|---|---|---|
| 3 | 4.5 | 26.9 | 10.1 | 34.3 | 71.3 | 30 |
| 4 | 6 | 12.5 | 0.4 | 4.3 | 17.2 | 6 |
| 5 | 5.5 | 20.1 | 1.2 | 5.2 | 26.5 | 11 |

The results shown in Table II demonstrate that the invention run (No. 3) gave significantly better yields of the diacetoxy butenes than either of the control runs (Nos. 4 and 5).

EXAMPLE III

Other runs were conducted according to the instant invention utilizing iodosobenzene diacetate in the presence of lithium bromide for the oxidation of 1,3-butadiene. The runs of this Example also demonstrate the effect of the amount of lithium bromide present on the yield of the diacetoxy butenes and also illustrate the yield promoting effect of the alkali metal bromide component by utilizing lithium acetate in one of the runs. Other runs are also presented in this Example which utilize vanadium pentoxide instead of an alkali metal bromide component.

The runs of this Example were also carried out utilizing the 250 ml Fisher-Porter aerosol compatibility bottle as the reaction vessel for the runs. In each run, the reaction vessel was charged with 6.4 grams (20 mmoles) of the iodosobenzene diacetate, the indicated amount from Table III of the lithium bromide or other compound, and either a mixture of acetic acid and acetic anhydride or acetic anhydride alone as the reaction diluent. The reaction vessel was then charged with the indicated amount of butadiene (Bd) from the vapor phase and the reaction vessel placed in an oil bath, pressured to 30 psig with oxygen and heated to 140° C. As in previous runs, the reaction vessel was pressured to about 120-130 psig with oxygen at about 20 minute intervals. The reaction mixture obtained from each run was handled in essentially the same manner as previously described and the yields of diacetoxy butenes obtained in each run are presented in Table III below Comparison of the results obtained in Runs 6 and 7 above demonstrate the effect of excessive amounts of lithium bromide on the desired oxidation reaction. However, comparison of Run No. 6 with Run No. 1 of Example I demonstrates the beneficial effect of lithium bromide in suitable amounts on the yield of the desired diacetoxy butenes in the process of the instant invention.

In the runs employing acetic anhydride alone as the reaction diluent, the influence of the alkali metal bromide is less clearly defined in comparison to the control run (No. 9). Although an analysis was not carried out on the recovered fraction comprising the diacetoxy butenes from Run No. 8, it is believed that the yield of diacetoxy butenes in said Run No. 8 is somewhat better than the yields for the closest comparable run, No. 9.

Due to an accident which occurred during the work-up of the reaction mixture from Run No. 10, it was not possible to obtain reliable analysis values for the product reaction mixture. Run No. 10 was repeated as Run No. 11. Although about 15 grams of a brown oil was obtained as the product fraction in Run No. 11, analysis of said brown oil was not carried out. It is believed, however, that the yield of diacetoxy butenes obtained in Run 11 was not as good as that obtained in Run No. 8 carried out according to the instant invention with acetic anhydride alone as the reaction diluent.

EXAMPLE IV

As a control run for the instant invention, a run was carried out in which a 250 ml Fisher-Porter aerosol compatibility bottle was charged with 4.9 grams (20 mmoles) of para-iodobenzoic acid, 100 ml of acetic anhydride and 12.0 grams (222 mmoles) of butadiene from the vapor phase. The reactor was charged to 30 psig with oxygen and heated to 140° C. as in the earlier runs. After about one hour, in order to reach the desired reaction temperature, the reaction vessel was pressured at about 20 minute intervals to 120 psig with oxygen. After 5 hours reaction at the indicated temperature, the reactor was cooled briefly, vented and weighed to determine the weight gain of the reaction mixture. The reaction mixture was filtered and the filtrate transferred to a distillation flask and distilled as previously described through an 18" Vigreaux column. Only 3.8 grams of the fraction boiling in the temperature range for the diacetoxy butenes was recovered in this run. This indicated a very low yield of the desired diacetoxy butenes and the fraction was not further analyzed. This result demonstrates the deleterious effect of the carboxy substituent on the aromatic iodine compound when utilized for the oxidation of 1,3-butadiene in the presence of oxygen.

EXAMPLE V

To demonstrate the effectiveness of the reaction system of this invention for the oxidation of a monoolefin, a one-liter stainless steel autoclave was charged with 300 ml of acetic anhydride, 6.4 grams (20 mmoles) of iodosobenzene diacetate and 53 grams (946.4 mmoles) of trans-2-butene. The reactor was pressured to 30 psig with oxygen and heated to 140° C. The reaction vessel was pressured from time to time with oxygen as in the earlier runs up to about 200 psig during about 2 hours of the three and one-half hours reaction period. At the conclusion of the reaction, the autoclave was vented and the reaction mixture transferred to a distillation flask utilizing a little acetic anhydride as a rinsing solvent for the reaction vessel. The mixture was distilled through a ¾" (1.91 cm)×15" (39 cm) column packed with 6 millimeter Raschig rings. Four fractions were collected during the distillation procedure. Analysis by gas-liquid phase chromatography of fractions 3 to 4 indicated that 217.2 mmoles of 2,3-diacetoxy butane were obtained for a yield of 23 percent based on the starting trans-2-butene. This result demonstrates that iodosobenzene diacetate in the presence of oxygen does effect the oxidation of a monoolefin to a diacyloxy alkane product.

What I claim is:

1. In a process for producing esters by
contacting at least one olefin selected from the group consisting of substituted or unsubstituted monoolefins, substituted or unsubstituted diolefins and mixtures thereof; at least one iodosoaryl dicarboxylate and at least one compound selected from the group consisting of carboxylic acids, carboxylic acid anhydrides and mixtures thereof; the improvement comprising employing in said process oxygen at a pressure within the range of about 0.1 to about 1000 psig above autogenous pressure at the temperature employed; and a source of bromide ion wherein the atom ratio of bromide ion to iodide is within the range of from about 1:1 to about 5:1 to form a reaction mixture which is subjected to suitable reaction conditions to produce a corresponding ester.

2. A process in accordance with claim 1 wherein said monoolefin is an acyclic monoolefin of 2 to 16 carbon atoms per molecule, and said ester comprises diacyloxy alkanes.

3. A process according to claim 2 wherein said acyclic monoolefin is represented by the following general formula

(I)

wherein R is individually selected from the group consisting of hydrogen, halogen, cyano, —COOR', and a hydrocarbyl radical comprising 1 to 12 carbon atoms and selected from the group consisting of alkyl, aryl, cycloalkyl, aralkyl and alkaryl radicals, and R' is selected from the group consisting of hydrogen, alkyl radicals having 1 to 10 carbon atoms, and aryl radicals having 6 to 10 carbon atoms.

4. A process according to claim 2 wherein said acyclic monoolefin is ethylene, propylene, 1-butene, 2-butene, 1-hexene, 2-octene, 1-decene, 3-dodecene, 1-hexadecene, 2,3-dimethyl-2-butene, vinylcyclohexane, 1,1-diphenylethylene, 1-chloro-2-butene, 3-butenenitrile, or ethyl cinnamate.

5. A process in accordance with claim 1 wherein said monoolefin is a cyclic monoolefin of 4 to about 16 carbon atoms per molecule, and said diester comprises diacyloxy cycloalkanes.

6. A process according to claim 5 wherein said cyclic monoolefin is represented by the following general formula

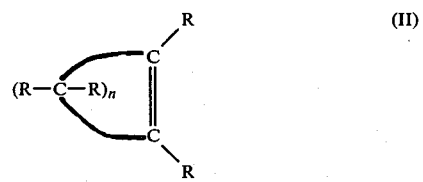
(II)

wherein R is individually selected from the group consisting of hydrogen, halogen, cyano, —COOR', and a hydrocarbyl radical comprising 1 to 12 carbon atoms and selected from the group consisting of alkyl, aryl, cycloalkyl, aralkyl and alkaryl radicals, and R' is selected from the group consisting of hydrogen, alkyl radicals having 1 to 10 carbon atoms, and aryl radicals having 6 to 10 carbon atoms and wherein n is an integer of from 1 to 14.

7. A process according to claim 5 wherein said cyclic monoolefin is cyclobutene, cyclopentene, cyclohexene, cycloheptene, cyclooctene, cyclododecene, 1-methyl-1-cyclopentene, 1-phenyl-1-cyclohexene, ethyl 1-cyclohexene-1-carboxylate, 1,3,4,5,6-pentachlorocyclohexene, or 1-cyano-1-cyclohexene.

8. A process according to claim 1 wherein said diolefin is an acyclic conjugated diolefin of 4 to about 16 carbon atoms per molecule, and wherein said diester comprises diacyloxy acyclic olefins.

9. A process according to claim 8 wherein said acyclic conjugated diolefin is represented by the following general formula

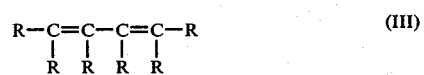
(III)

wherein R is individually selected from the group consisting of hydrogen, halogen, cyano, —COOR', and a hydrocarbyl radical comprising 1 to 12 carbon atoms and selected from the group consisting of alkyl, aryl, cycloalkyl, aralkyl and alkaryl radicals, and R' is selected from the group consisting of hydrogen, alkyl radicals having 1 to 10 carbon atoms, and aryl radicals having 6 to 10 carbon atoms.

10. A process according to claim 8 wherein said acyclic conjugated diolefin is 1,3-butadiene, 2-methyl-1,3-butadiene, 2-chloro-1,3-butadiene, 2-ethyl-1,3-butadiene, 2-cyano-1,3-butadiene, 2-methylene-3-butenoic acid, 2,4-pentadienenitrile, 1,3-hexadecadiene, 2-methoxycarbonyl-1,3-butadiene, 2-decycloxycarbonyl-1,3-butadiene, 2-phenoxycarbonyl-1,3-butadiene, 2-(1-naphthyloxy)carbonyl-1,3-butadiene, 2-benzyl-1,3-butadiene, 2-p-tolyl-1,3-butadiene, or 2-chloro-3-methyl-1,3-butadiene.

11. A process according to claim 1 wherein said diolefin is a acyclic or cyclic non-conjugated diolefin.

12. A process according to claim 11 wherein said acyclic or cyclic non-conjugated diolefin is selected from the group consisting of 1,5-hexadiene, 1,7-octadiene, 1,9-decadiene, 1,4-cyclohexadiene, 1,5-cyclooctadiene, 1,5-cyclododecadiene and mixtures of any two or more thereof.

13. A process according to claim 1 wherein said diolefin is a cyclic conjugated diolefin of 5 to about 16 carbon atoms per molecule, and wherein said diester comprises diacyloxy cyclic olefins.

14. A process according to claim 13 wherein said cyclic conjugated diolefin is represented by the following general formula

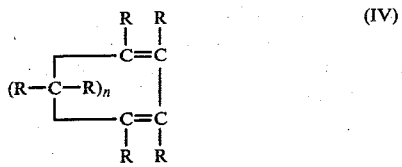

(IV)

wherein R is individually selected from the group consisting of hydrogen, halogen, cyano, —COOR', and a hydrocarbyl radical comprising 1 to 12 carbon atoms and selected from the group consisting of alkyl, aryl, cycloalkyl, aralkyl and alkaryl radicals, and R' is selected from the group consisting of hydrogen, alkyl radicals having 1 to 10 carbon atoms, and aryl radicals having 6 to 10 carbon atoms and wherein n is an integer of from 1 to 14.

15. A process according to claim 13 wherein said cyclic conjugated diolefin is 1,3-cyclohexadiene, 1,3-cyclooctadiene, 1,3-cyclododecadiene, 5-methyl-1,3-cyclohexadiene, 2,4-cyclohexadiene-1,2-dicarboxylic acid, octafluoro-1,3-cyclohexadiene, hexachlorocyclopentadiene, 5,6,7,8-tetrabromo-1,3-cyclooctadiene, 1,3-cyclohexadecadiene, 2-undecyl-1,3-cyclopentadiene, 2-methoxycarbonyl-1,3-cyclooctadiene, 2-decyloxycarbonyl-1,3-cyclopentadiene, 2-phenoxycarbonyl-1,3-cyclohexadiene, 2-(1-naphthyloxy)carbonyl-1,3-cyclopentadiene, 2-benzyl-1,3-cyclooctadiene, or 2-p-tolyl-1,3-cyclohexadiene.

16. A process according to claim 1 wherein said source of bromide ion is at least one of an alkali metal bromide.

17. A process according to claim 1 wherein the atom ratio of bromide ion to iodide is within the range of from about 2:1 to about 4:1.

18. A process according to claim 1 wherein the molar ratio of the total acyl moiety in the reaction mixture to the olefin reactant is at least 2:1.

19. A process according to claim 1 wherein the iodosoaryl dicarboxylate compound is represented by the following general formula:

(V)

wherein Ar— has from 6 to 12 carbon atoms and is selected from the group consisting of substituted or unsubstituted monocyclic aryl radical and dicyclic aryl radicals wherein said substituent is selected from the group consisting of alkyl, cycloalkyl, halo, carbalkoxy and cyano groups, and wherein said dicyclic aryl radicals are those having two monocyclic aryl moieties joined by only one carbon-carbon single bond, and wherein R" is selected from the group consisting of hydrocarbon radicals and halogen, cyano and —COOR' substituted derivatives thereof, wherein up to four of said halogen, cyano, or —COOR' substituents can be present in said R" radical, and wherein R' is selected from the group consisting of hydrogen, aryl radicals having 1 to 10 carbon atoms and aryl radicals having 6 to 10 carbon atoms.

20. A process according to claim 19 wherein said Ar radical is selected from the group consisting of phenyl, 4-methylphenyl, 4-hexylphenyl, 4-cyclohexylphenyl, 4-cyanophenyl, 4-chlorophenyl, 4-carbethoxyphenyl, 4-biphenyl, 3-biphenyl, 2-biphenyl, 3-isopropylphenyl, 3-bromophenyl, 4-fluorophenyl, 3-iodophenyl and 3-cyano-4-methylphenyl.

21. A process according to claim 19 wherein said iodosoaryl dicarboxylate is selected from the group consisting of iodosobenzene diacetate, iodosobenzene dihexanoate, iodosobenzene didodecanoate, iodosobenzene di(trichloroacetate), iodosobenzene di(4-cyanobenzoate), iodoso-4,4'-byphenyl diacetate, iodoso-4-cyclohexylphenyl diacetate, iodoso-3-isopropylphenyl diacetate, iodoso-3-bromophenyl diacetate, iodoso-3-cyano-4-methylphenyl diacetate, iodoso-4-methylphenyl diacetate, iodoso-4-cyanophenyl diacetate and mixtures of any two or more thereof.

22. A process according to claim 19 wherein the iodosoaryl dicarboxylate is iodosobenzene diacetate.

23. A process according to claim 1 wherein each of said carboxylic acid and said acid anhydride has from 2 to about 18 carbon atoms per molecule and is represented by the general formula R"—COOH and anhydrides thereof, wherein R" is selected from the group consisting of hydrocarbon radicals, and halogen, cyano and —COOR' substituted derivatives thereof, wherein up to four of said halogen, cyano or —COOR' substituents can be present in said radical, and R' is selected from the group consisting of hydrogen, an alkyl radical of 1 to 10 carbon atoms, and an aryl radical of 6 to 10 carbon atoms.

24. A process according to claim 23 wherein said carboxylic acid and acid anhydride is selected from the group consisting of acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, 2-bromobutanoic acid, ethyl hydrogen adipate, 2-chlorobenzoic acid, 4-cyanobenzoic acid, 2,3,4,5-tetrachlorobenzoic acid, ethyl hydrogen-o-phthalate, 4,6,8,10-tetracyanoundecanoic acid, 4,6,8,10-tetramethoxycarbonylundecanoic acid, 4-decyloxycarbonylcyclohexanecarboxylic acid, and acid anhydrides thereof.

25. A process according to claim 1 which is carried out at a temperature within a range of about 70° C. to about 170° C., an oxygen pressure within a range of about 0.1 to 1000 psig above autogenous pressure and a reaction time within a range of about 1 minute to about 12 hours.

26. A process according to claim 1 which is carried out at a temperature within a range of about 90° C. to about 150° C., an oxygen pressure within a range of about 5 to about 200 psig above autogenous pressure and a reaction time within a range of about 1 minute to about 12 hours.

27. A process according to claim 1 wherein the diolefin is 1,3-butadiene, the iodosoaryl dicarboxylate is iodosobenzene diacetate, and the carboxylic acid is acetic acid.

28. A process according to claim 27 wherein the carboxylic acid anhydride is acetic anhydride used in combination with acetic acid.

29. A process according to claim 1 wherein at least one carboxylic acid and at least one carboxylic acid anhydride corresponding to the carboxylic acid are employed.

30. A process according to claim 1 which is carried out in the liquid phase.

31. A process according to claim 1 wherein the iodosoaryl dicarboxylate present in the reaction mixture is formed in situ by the addition of ArI which reacts with the at least one compound selected from the group consisting of carboxylic acids, carboxylic acid anhydrides and mixtures thereof.

32. A process according to claim 31 wherein the ArI present in the reaction mixture is formed in situ by the addition of an aryl hydrocarbon and elemental iodine.

33. A process according to claim 31 wherein the diolefin is 1,3-butadiene, the ArI is iodobenzene, the carboxylic acid is acetic acid, and the carboxylic acid anhydride is acetic anhydride.

34. A process according to claim 33 which is carried out in the presence of lithium bromide.

35. A process according to claim 1 wherein the diolefin is 1,3-butadiene, the iodosoaryl dicarboxylate is iodosobenzene diacetate, the carboxylic acid is acetic acid, the reaction temperature employed is within a range of about 90° C. to about 150° C., the oxygen pressure employed is within a range of about 5 to about 200 psig above autogenous pressure and the reaction time employed is within a range of about 1 minute to about 12 hours.

36. A process according to claim 35 which is carried out in the presence of lithium bromide wherein the molar ratio of bromide ion to iodosoarylbenzene diacetate is sufficient to provide enhanced yields of the desired diacyloxy olefins.

37. In a process for producing esters from at least one olefin selected from the group consisting of substituted or unsubstituted monoolefins, substituted or unsubstituted diolefins and mixtures thereof, the improvement comprising contacting said at least one olefin with a mixture consisting essentially of oxygen at a pressure within the range of about 0.1 to about 1000 psig above autogenous pressure at the temperature employed, at least one iodoso aryl dicarboxylate, and at least one compound selected from the group consisting of carboxylic acids, carboxylic acid anhydrides and mixtures thereof under suitable reaction conditions to produce a corresponding ester from the at least one olefin.

38. A process in accordance with claim 37 wherein said monoolefin is an acyclic monoolefin of 2 to 16 carbon atoms per molecule, and said ester comprises diacyloxy alkanes.

39. A process according to claim 38 wherein said acyclic monoolefin is represented by the following general formula

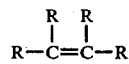

(I)

wherein R is individually selected from the group consisting of hydrogen, halogen, cyano, —COOR', and a hydrocarbyl radical comprising 1 to 12 carbon atoms and selected from the group consisting of alkyl, aryl, cycloalkyl, aralkyl and alkaryl radicals, and R' is selected from the group consisting of hydrogen, alkyl radicals having 1 to 10 carbon atoms, and aryl radicals having 6 to 10 carbon atoms.

40. A process according to claim 38 wherein said acyclic monoolefin is ethylene, propylene, 1-butene, 2-butene, 1-hexene, 2-octene, 1-decene, 3-dodecene, 1-hexadecene, 2,3-dimethyl-2-butene, vinylcyclohexane, 1,1-diphenylethylene, 1-chloro-2-butene, 3-butenenitrile, or ethyl cinnamate.

41. A process in accordance with claim 37 wherein said monoolefin is a cyclic monoolefin of 4 to about 16 carbon atoms per molecule, and said diester comprises diacyloxy cycloalkanes.

42. A process according to claim 41 wherein said cyclic monoolefin is represented by the following general formula

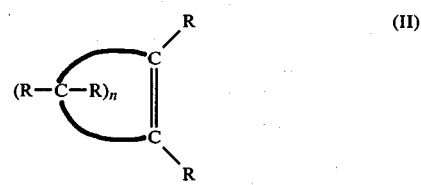

wherein R is individually selected from the group consisting of hydrogen, halogen, cyano, —COOR', and a hydrocarbyl radical comprising 1 to 12 carbon atoms and selected from the group consisting of alkyl, aryl, cycloalkyl, aralkyl and alkaryl radicals, and R' is selected from the group consisting of hydrogen, alkyl radicals having 1 to 10 carbon atoms, and aryl radicals having 6 to 10 carbon atoms and wherein n is an integer of from 1 to 14.

43. A process according to claim 41 wherein said cyclic monoolefin is cyclobutene, cyclopentene, cyclohexene, cycloheptene, cyclooctene, cyclododecene, 1-methyl-1-cyclopentene, 1-phenyl-1-cyclohexene, ethyl 1-cyclohexene-1-carboxylate, 1,3,4,5,6-pentachlorocyclohexene, or 1-cyano-1-cyclohexene.

44. A process according to claim 37 wherein said diolefin is an acyclic conjugated diolefin of 4 to about 16 carbon atoms per molecule, and wherein said diester comprises diacyloxy acyclic olefins.

45. A process according to claim 44 wherein said acyclic conjugated diolefin is represented by the following general formula

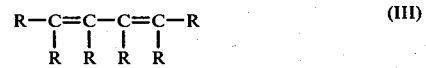

wherein R is individually selected from the group consisting of hydrogen, halogen, cyano, —COOR', and a hydrocarbyl radical comprising 1 to 12 carbon atoms and selected from the group consisting of alkyl, aryl, cycloalkyl, aralkyl and alkaryl radicals, and R' is selected from the group consisting of hydrogen, alkyl radicals having 1 to 10 carbon atoms, and aryl radicals having 6 to 10 carbon atoms.

46. A process according to claim 44 wherein said acyclic conjugated diolefin is 1,3-butadiene, 2-methyl-1,3-butadiene, 2-chloro-1,3-butadiene, 2-ethyl-1,3-butadiene, 2-cyano-1,3-butadiene, 2-methylene-2-butenoic acid, 2,4-pentadienenitrile, 1,3-hexadecadiene, 2-methoxycarbonyl-1,3-butadiene, 2-decycloxycarbonyl-1,3-butadiene, 2-phenoxycarbonyl-1,3-butadiene, 2-(1-naphthyloxy)carbonyl-1,3-butadiene, 2-benzyl-1,3- butadiene, 2-p-tolyl-1,3-butadiene, or 2-chloro-3-methyl-1,3-butadiene.

47. A process according to claim 37 wherein said diolefin is an acyclic or cyclic non-conjugated diolefin.

48. A process according to claim 47 wherein said acyclic or cyclic non-conjugated diolefin is selected from the group consisting of 1,5-hexadiene, 1,7-octadiene, 1,9-decadiene, 1,4-cyclohexadiene, 1,5-cyclooctadiene, 1,5-cyclododecadiene and mixture of any two or more thereof.

49. A process according to claim 37 wherein said diolefin is a cyclic conjugated diolefin of 5 to about 16 carbon atoms per molecule, and wherein said diester comprises diacyloxy cyclic olefins.

50. A process according to claim 49 wherein said cyclic conjugated diolefin is represented by the following general formula

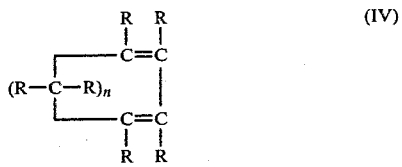

wherein R is individually selected from the group consisting of hydrogen, halogen, cyano, —COOR', and a hydrocarbyl radical comprising 1 to 12 carbon atoms and selected from the group consisting of alkyl, aryl, cycloalkyl, aralkyl and alkaryl radicals, and R' is selected from the group consisting of hydrogen, alkyl radicals having 1 to 10 carbon atoms, and aryl radicals having 6 to 10 carbon atoms and wherein n is an integer of from 1 to 14.

51. A process according to claim 49 wherein said cyclic conjugated diolefin is 1,3-cyclohexadiene, 1,3-cyclooctadiene, 1,3-cyclododecadiene, 5-methyl-1,3-cyclohexadiene, 2,4-cyclohexadiene-1,2-dicarboxylic acid, octafluoro-1,3-cyclohexadiene, hexachlorocyclopentadiene, 5,6,7,8-tetrabromo-1,3-cyclooctadiene, 1,3-cyclohexadecadiene, 2-undecyl-1,3-cyclopentadiene, 2-methoxycarbonyl-1,3-cyclooctadiene, 2-decyloxycarbonyl-1,3-cyclopentadiene, 2-phenoxycarbonyl-1,3-cyclohexadiene, 2-(1-naphthyloxy)carbonyl-1,3-cyclopentadiene, 2-benzyl-1,3-cyclooctadiene, or 2-p-tolyl-1,3-cyclohexadiene.

52. A process according to claim 37 wherein the molar ratio of the total acyl moiety in the reaction mixture to the olefin reactant is at least 2:1.

53. A process according to claim 37 wherein the iodosoaryl dicarboxylate compound is represented by the following general formula:

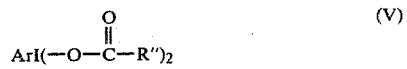

wherein Ar— has from 6 to 12 carbon atoms and is selected from the group consisting of substituted or unsubstituted monocyclic aryl radical and dicyclic aryl radicals wherein said substituent is selected from the group consisting of alkyl, cycloalkyl, halo, carbalkoxy and cyano groups, and wherein said dicyclic aryl radicals are those having two monocyclic aryl moieties joined by only one carbon-carbon single bond, and wherein R' is selected from the group consisting of hydrocarbon radicals and halogen, cyano and —COOR' substituted derivatives thereof, wherein up to four of said halogen, cyano, or —COOR' substituents can be present in said R" radical, and wherein R' is selected from the group consisting of hydrogen, alkyl radicals having 1 to 10 carbon atoms and aryl radicals having 6 to 10 carbon atoms.

54. A process according to claim 53 wherein said Ar radical is selected from the group consisting of phenyl, 4-methylphenyl, 4-hexylphenyl, 4-cyclohexylphenyl, 4-cyanophenyl, 4-chlorophenyl, 4-carbethoxyphenyl, 4-biphenyl, 3-biphenyl, 2-biphenyl, 3-isopropylphenyl, 3-bromophenyl, 4-fluorophenyl, 3-iodophenyl and 3-cyano-4-methylphenyl.

55. A process according to claim 53 wherein said iodosoaryl dicarboxylate is selected from the group consisting of iodosobenzene diacetate, iodosobenzene dihexanoate, iodosobenzene didodecanate, iodosobenzene di(trichloroacetate), iodosobenzene di(4-cyanobenzoate), iodoso-4,4'-byphenyl diacetate, iodoso-4-cyclohexylphenyl diacetate, iodoso-3-isopropylphenyl diacetate, iodoso-3-bromophenyl diacetate, iodoso-3-cyano-4-methylphenyl diacetate, iodoso-4-methylphenyl diacetate, iodoso-4-cyanophenyl diacetate and mixtures of any two or more thereof.

56. A process according to claim 53 wherein the iodosoaryl dicarboxylate is iodosobenzene diacetate.

57. A process according to claim 37 wherein each of said carboxylic acid and said acid anhydride has from 2 to about 18 carbon atoms per molecule and is represented by the general formula R"—COOH and anhydrides thereof, wherein R' is selected from the group consisting of hydrocarbon radicals, and halogen, cyano and —COOR' substituted derivatives thereof, wherein up to four of said halogen, cyano or —COOR' substituents can be present in said radical, and R' is selected from the group consisting of hydrogen, an alkyl radical of 1 to 10 carbon atoms, and an aryl radical of 6 to 10 carbon atoms.

58. A process according to claim 57 wherein said carboxylic acid and acid anhydride is selected from the group consisting of acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, 2-bromobutanoic acid, ethyl hydrogen adipate, 4-chlorobenzoic acid, 4-cyanobenzoic acid, 2,3,4,5-tetrachlorobenzoic acid, ethyl hydrogen-o-phthalate, 4,6,8,10-tetracyanoundecanoic acid, 4,6,8,10-tetramethoxycarbonylundecanoic acid, 4-decyloxycarbonylcyclohexanecarboxylic acid, and acid anhydrides thereof.

59. A process according to claim 37 which is carried out at a temperature within a range of about 90° C. to about 150° C., an oxygen pressure within a range of about 5 to about 200 psig above autogenous pressure and a reaction time within a range of about 1 minute to about 12 hours.

60. A process according to claim 37 wherein the diolefin is 1,3-butadiene, the iodosoaryl dicarboxylate is iodosobenzene diacetate, and the carboxylic acid is acetic acid.

61. A process according to claim 60 wherein the carboxylic acid anhydride is acetic anhydride used in combination with acetic acid.

62. A process according to claim 37 wherein at least one carboxylic acid and at least one carboxylic acid anhydride corresponding to the carboxylic acid are employed.

63. A process according to claim 37 which is carried out in the liquid phase.

64. A process according to claim 37 wherein the iodosoaryl dicarboxylate present in the reaction mixture is formed in situ by the addition of ArI which reacts with the at least one compound selected from the group consisting of carboxylic acids, carboxylic acid anhydrides and mixtures thereof.

* * * * *

UNITED STATES PATENT AND TRADEMARK OFFICE
CERTIFICATE OF CORRECTION

PATENT NO.   :   4,221,917
DATED        :   September 9, 1980
INVENTOR(S)  :   Paul R. Stapp It is certified that error appears in the above-identified patent and that said Letters Patent are hereby corrected as shown below:

Column 14, line 2, "aryl" should read --- alkyl ---; line 47, after "adipate," "2-" should read --- 4- ---;

Column 16, line 64, "2-methylene-2-" should read --- 2-methylene-3 ---.

Signed and Sealed this

Twenty-fifth Day of November 1980

[SEAL]

Attest:

SIDNEY A. DIAMOND

Attesting Officer

Commissioner of Patents and Trademarks